(12) United States Patent
Grant

(10) Patent No.: US 6,852,688 B2
(45) Date of Patent: Feb. 8, 2005

(54) COMPOSITIONS FOR TREATING DIABETIC RETINOPATHY AND METHODS OF USING SAME

(75) Inventor: Maria Grant, Gainesville, FL (US)

(73) Assignee: University of Florida, Gainesville, FL (US)

(*) Notice: Subject to any disclaimer, the term of this patent is extended or adjusted under 35 U.S.C. 154(b) by 0 days.

(21) Appl. No.: 09/804,484

(22) Filed: Mar. 12, 2001

(65) Prior Publication Data

US 2002/0045569 A1 Apr. 18, 2002

Related U.S. Application Data

(60) Provisional application No. 60/188,483, filed on Mar. 10, 2000.

(51) Int. Cl.⁷ ..................... A61K 31/198; A61K 38/22; A61K 38/31
(52) U.S. Cl. .............................. 514/8; 514/11; 514/14; 514/16; 514/51; 514/567
(58) Field of Search ................................ 514/8, 11, 14, 514/16, 21, 567; 530/311, 397; 564/447; 562/447

(56) References Cited

U.S. PATENT DOCUMENTS

| | | | |
|---|---|---|---|
| 4,863,457 A | 9/1989 | Lee | 604/891.1 |
| 4,997,652 A | 3/1991 | Wong | 424/428 |
| 5,098,443 A | 3/1992 | Parel et al. | 623/4 |
| 5,164,188 A | 11/1992 | Wong | 424/428 |
| 5,185,152 A | 2/1993 | Peyman | 424/427 |
| 5,378,475 A | 1/1995 | Smith et al. | 424/473 |
| 5,384,333 A | 1/1995 | Davis et al. | 514/772.3 |
| 5,443,505 A | 8/1995 | Wong et al. | 623/4 |
| 5,554,187 A | 9/1996 | Rizzo, III | 623/6 |
| 5,583,224 A | 12/1996 | Riese | 299/13 |
| 5,710,145 A | 1/1998 | Engel et al. | 514/183 |
| 5,710,182 A | 1/1998 | Reunamaki et al. | 514/772.3 |
| 5,718,922 A | 2/1998 | Herrero-Vanrell et al. | 424/501 |
| 5,719,175 A | 2/1998 | Heath, Jr. et al. | 514/410 |
| 5,725,493 A | 3/1998 | Avery et al. | 604/9 |
| 5,919,813 A | 7/1999 | De Juan, Jr. | 514/432 |
| 6,440,933 B1 * | 8/2002 | Bodor et al. | 514/11 |

OTHER PUBLICATIONS

Grant et al. Octreotide Retards Progression of Diabetic Retinopathy in Patients Treated with Thyroid Hormone. Diabetes. 1999, vol. 48, Suppl. 1, pp. A155–A156, Abstract No. 0674.*

Anonymous, *MMWR* (1993) 42(10): 191–195.

Plewe, G. et al. "Somatostatin analogue SMS 201–995 in type I diabetes mellitus. Initial experience after repeated administration." *Scand J Gastroenterol Suppl.* (1986) 119: 166–169.

Klein, et al. *Opthalmol.* (1984) 91: 10–17.

Merimee, T.J. *New England Journal of Medicine.* (1990) 322: 978–983.

Murphy, *American Family Physician* (1995) 51(4): 785–796.

Rohrer, et al. "Rapid identification of subtype–selective agonists of the somatostatin receptor through combinatorial chemistry" *Science.* (1998) 282: 737–740.

(List continued on next page.)

*Primary Examiner*—Jeffrey Edwin Russel
(74) *Attorney, Agent, or Firm*—Timothy H. Van Dyke; Beusse Brownlee Wolter Mora & Maire (57) ABSTRACT

The subject invention provides novel methods and materials for treating diabetic retinopathy. One embodiment of the subject invention involves the co-administration of a somatostatin, or analogue thereof, and a thyroid-related substance such as thyroxine. Somatostatin or thyroid-related substance can be administered in combination, or separately through the same or different modes of administration.

15 Claims, 3 Drawing Sheets

OTHER PUBLICATIONS

*ASHP Handbook on Injectable Drugs.* Trissel, 4$^{th}$ ed. (1986) 622–630.

Aiello, et al. *PNAS USA.* (1995) 92: 10457–10461.

DHAR, et al., *Mol. Pharmacol.* (1990) 37: 519–525.

Asahi, et al. *FEBS Letter.* (1992) 309: 10–14.

Tomlinson, et al. *Pharmac. Ther.* (1992) 54: 151–194.

The Diabetic Retinopathy Study Research Group "Indications for photocoagulation treatment of diabetic retinopathy: Diabetic Retinopathy Study Report No: 14" *Int. Opthalmol. Clin.* (1987) 27: 239.

Early Treatment Diabetic Retinopathy Study Research Group "Techniques for scatter and local photocoagulation treatment of diabetic retinopathy. Early Treatment Diabetic Research Study Report No. 3" *Int. Opthamol Clin.* (1987) 27: 254–264.

Kirkegaard, et al. "Effect of one year continuous subcutaneous infusion of a somatostatin analogue, octreotide, on early retinopathy, metabolic control and thyroid function in Type–1 (insulin–dependent) diabetes mellitus" *Acta Endocrinol* (Copenh) (1990) 122: 766–72.

Colas, et al., "Stimulation of a membrane tyrosine phosphatase activity by somatostatin analogues in rat pancreatic acinar cells" *Eur. J. Biochem.* (1992) 207: 1017–1024.

Leszczynski, et al. "Rat heart smooth muscle cells express high and low affinity receptors for somatostatin–14, which are involved in regulation of cell proliferation" *Life Sci.* (1993) 53: 1663–1674.

Grant, et al. "Inhibition of IGF–I and b–FGF stimulated growth of human retinal endothelial cells by the somatostatin analogue, octreotide: a potential treatment for ocular neovascularization" *Regul Pept* (1993) 48: 267–278.

Grant, et al. *Diabetes.* (1986) 35: 416–420.

Meyer–Schwickerath, et al. *J. Clin. Invest.* (1993) 92: 2620–2625.

Grant, et al. *Ann Ny Acad Science.* (1993) 692: 230–242.

Danis, et al. *Opthalmology.* (1997) 104: 1661–1669.

Amiel, et al. *Diabetes.* (1984) 33: 1175–1179.

Tan, et al. *J. Clin. Endocrinol. Metab.* (1986) 63: 651–655.

Kolaczynski, et al. *Ann Inern Med.* (1994) 120: 47–55.

Langford, et al. *Eur. J. Clin. Invest.* (1993) 23: 503–516.

Koller, et al. *J. Clin Endocrinol Metab.* (1998) 83: 2380–2383.

Aiello, et al. *Diabetes.* (1997) 46: 1473–1480.

Smith, et al. *Science.* (1997) 276: 1706–1709.

McCombe, M. et al. "Effect of long–acting somatostatin analogue (BIM23014) on proliferative diabetic retinopathy: a pilot study" *Eye* (1991) 5: 569–575.

\* cited by examiner

Figure 3  PRP survival curves from Phase I (top panel) and Phase II (bottom panel). Phase I results showed no significant difference in survival time before requiring PRP between conventional diabetes management (control, n=8) and patients treated with maximally tolerated doses of octreotide (OCT, 600-3000 µg/day, n=8). Phase II results showed highly significant differences for survival of individual eyes to laser treatment for control, (n=22) and octreotide + thyroxine treatment (OCT+$T_4$, n=24).

COMPOSITIONS FOR TREATING DIABETIC RETINOPATHY AND METHODS OF USING SAME

CROSS-REFERENCE TO RELATED APPLICATIONS

This application claims the benefit under 35 USC §119(e) of Provisional Application No. 60/188,483 filed Mar. 10, 2000.

BACKGROUND OF THE INVENTION

More than 14 million people in the United States have diabetes. All people with diabetes are at risk of retinal complications. However, people with type I, i.e., insulin-dependent, diabetes, face a greater risk of severe vision loss than people with type II, i.e., non-insulin dependent, diabetes. Initially, the high blood glucose level in diabetic people causes an increase in growth factors in their eyes. This condition is known as the "pre-diabetic retinopathy stage" and can lead to retinopathy, if not prophylactically treated.

Retinopathy will affect the majority of diabetic people to some extent during their lifetimes (Anonymous, MMWR 42(10): 191–195 (1993)). It is the leading cause of blindness in Americans of age 20 to 74 today and is expected to impair vision in approximately one-third of diabetic people in the United States. Each year in the United States, as many as 40,000 new cases of blindness occur among diabetic people. Diabetic people are 25 times more likely than the general population to become blind due to retinopathy.

Diabetic retinopathy (DR) is recognized as a retinal vascular disorder that includes: (1) excess capillary permeability, (2) vascular closure, and (3) proliferation of new vessels (Council NAE. Report of the Retinal Diseases Panel. Vision Research: A National Plan 1994–1998. Vol. NIH Publication No. 93-3186. Bethesda: Public Health Service, 1993:11–109.). DR is recognized to consist of two (2) stages: nonproliferative and proliferative. In the nonproliferative stage the disease is characterized by a loss of retinal capillary pericytes, thickening of the basement membrane and development of microaneurysms, dot-blot hemorrhages, and hard exudates. In the proliferative stage the disease patients develop extensive neovascularization, vessel intrusion into the vitreous, bleeding and fibrosis with subsequent retinal traction, which leads to severe vision impairment (Klein et al., *Opthalmol*, (1984); 91:10–17. Merimee T. J., *New England Journal of Medicine* 322:978–987(1990)).

While the pathological stages of diabetic retinopathy are well-described, the molecular events underlying diabetic retinopathy are poorly understood. This is due, in part, to the fact that the disease progresses over ten to thirty years, depending on a given individual. Tight control of glycemia and hypertension and ophthalmic screening of diabetics appears beneficial in preventing the disease. Current treatment consists of regular observation by an ophthalmologist, laser photocoagulation and vitrectomy.

Macular edema threatening or involving the macular center is treated with focal macular photocoagulation. Small (50 microns in diameter), mild-intensity laser burns are targeted at areas of leakage in the macula (Murphy, *Amer. Family Physician* 51(4): 785–796 (1995)). If the macular edema persists, retreatment may be necessary. Patients with severe to very severe nonproliferative retinopathy and patients, who are at high risk for proliferative retinopathy or who already have early or advanced proliferative retinopathy, are treated with scatter or panretinal photocoagulation. Panretinal photocoagulation (PRP) involves 1,500–2,000 laser burns, which are 500 microns in diameter, in the midperipheral and peripheral portion of the retina (Murphy (1995), supra). In light of the prevalence of DR, there remains a need for therapeutic and prophylactic treatments for this disease.

SUMMARY OF THE INVENTION

The subject invention is directed to novel treatment for diabetic retinopathy (DR). According to a specific aspect the subject invention pertains to a method of treating DR comprising administering a somatostatin alone, or co-administering a thyroid-related substance in a patient in need thereof.

According to another aspect, the subject invention pertains to a composition containing both somatostatin and a thyroid-related substance.

According to a further aspect, the subject invention pertains to a method of treating DR comprising assaying a group of somatostatin analogues for their ability to bind to the sstr2 somatostatin receptor; selecting one or more analogues having high affinity to the sstr2 somatostatin receptor; and administering said one or more selected analogues to a patient in need thereof. Preferably, the one or more selected analogues have a $K_i$ value (nanomoles) of 2 or less. See Rohrer et al., *Science* 282:737–740 (1998). Patients who do not favorably respond to administration of the somatostatin analogue alone, preferably are treated by co-administration of a TRS.

According to a further aspect, the subject invention pertains to a kit comprising at least one container having somatostatin and/or a thyroid-related substance therein. Preferably, the kit contains a syringe for administration of the somatostatin and/or thyroid-related substance. More preferably, at least one container is one or more syringes having somatostatin and/or thyroid-related substance disposed in either one syringe as a mixture or in separate syringes. Alternatively, the somatostatin and/or thryroid-related substance is in form suitable for oral administration.

These and other advantageous aspects of the subject invention are described below.

DETAILED DESCRIPTION OF THE PREFERRED EMBODIMENTS

The term "co-administration" or "co-administering" as used herein refer to the administration of a substance before, concurrently, or after the administration of another substance such that the biological effects of either substance synergistically overlap.

The terms "thyroid-related substance" or "TRS" as used herein refers to thyroid hormone, thyroxine, thyrotropin, thyroid stimulating hormone, or analogues or, pharmaceutically acceptable salts or derivatives thereof that have similar biological functionality or effect in the body.

The term "somatostatin" as used herein refers to somatostatin as understood in the art or any derivative, pharmaceutically acceptable salt, or analogue thereof having somatostatin activity. Examples of somotostatin analogues contemplated for use in accord with the teachings herein include, but are not limited to peptide or non-peptide compounds, including but not limited to: octreotide, lanreotide, vapreotide, MK 678 (CAS No.81377-02-9), RC160 (CAS No. 103222-11-3), SRIF-14 (CAS No. 51110-01-1), SRIF-28 (CAS No. 75037-27-3), L-363-377, L-797, 591, L-779,976, L-796-778, L-803,087, and L-817,818. (See Rohrer et al., *Science,* 282:737–740 (1998)). Somatostatin analogues that are preferably used are those having increased binding affinities to sstr2. See Rohrer et al., supra; Patel and Srikant, Endocrinology, 135(6):2814–7 (1994). In a preferred embodiment, octreotide, L-797,976 or L-363, 377 is used as the somatostatin analogue.

Thyroid-related substances and somatostatin are widely available commercially. Those compounds that are not commercially available can be readily prepared using organic synthesis methods known in the art. Analogues, prodrugs and pharmaceutically acceptable salts of thyroid-related substances and somatostatin can be tested by in vitro studies of endothelial cell proliferation and in other models of diabetic retinopathy, such as Streptozotocin.

In addition, color Doppler imaging can be used to evaluate the action of a drug in ocular pathology (Valli et al., *Ophthalmologica* 209(13): 115–121 (1995)). Color Doppler imaging is a recent advance in ultrasonography, allowing simultaneous two-dimension imaging of structures and the evaluation of blood flow. Accordingly, retinopathy can be analyzed using such technology.

TRS or somatostatin can be bound to a suitable matrix, such as a polymeric matrix, if desired, for use in the present inventive method. Any of a wide range of polymers can be used in the context of the present invention provided that, if the polymer-bound compound is to be used in vivo, the polymer is biologically acceptable (see, e.g., U.S. Pat. Nos. 5,384,333 and 5,164,188). TRS and somatostatin can be administered in accord with the present inventive method by any suitable route. Suitable routes of administration include systemic, such as orally or by injection, topical, intraocular, periocular (e.g., subTenon's), subconjunctival, subretinal, suprachoroidal and retrobulbar.

Preferably, TRS and somatostatin is administered as soon as the pre-diabetic retinopathy state is detected. TRS and somatostatin can be administered separately or in combination. For example, somatostatin can be administered by injection and TRS can be administered orally or vice versa, or both orally, or both by injection or by some other form of administration. Preferably, they are administered as soon as possible after it has been determined that an animal, such as a mammal, specifically a human, is at risk for retinopathy (prophylactic treatment) or has begun to develop retinopathy (therapeutic treatment). Treatment will depend, in part, upon the particular compounds used, the amount of the compounds administered, the route of administration, and the cause and extent, if any, of retinopathy realized.

One skilled in the art will appreciate that suitable methods of administering a TRS and/or somatostatin, which are useful in the present inventive method, are available. Although more than one route can be used to administer a particular compound, a particular route can provide a more immediate and more effective reaction than another route. Accordingly, the described routes of administration are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors, including the strength of the particular compositions employed, the age, species, condition or disease state, and body weight of the animal, as well as the amount of the retina about to be affected or actually affected by retinopathy. The size of the dose also will be determined by the route, timing and frequency of administration as well as the existence, nature, and extent of any adverse side effects that might accompany the administration of a particular composition and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of either somostoatin or TRS in a dosage amount of from about 0.05 mg/kg/day to about 5 mg/kg/day, preferably from about 0.5 mg/kg/day to about 3 mg/kg/day, if administered systemically. Intraocular administration typically will involve the administration of from about 0.1 mg total to about 5 mg total, preferably from about 0.5 mg total to about 1 mg total. A preferred concentration for topical administration is 100 $\mu$M.

Compositions for use in the present inventive method preferably comprise a pharmaceutically acceptable carrier and an amount of somatostatin and/or TRS sufficient to treat retinopathy prophylactically or therapeutically. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, somatostatin and/or TRS can be formulated as polymeric compositions, inclusion complexes, such as cyclodextrin inclusion complexes, liposomes, microspheres, microcapsules and the like (see, e.g., U.S. Pat. Nos. 4,997,652, 5,185,152 and 5,718,922).

Somatostatin and TRS can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the somatostatin analogue or thyroid hormone and one which has no detrimental side effects or toxicity under the conditions of use.

The choice of excipient will be determined in part by the particular somatostatin analogue and/or thyroid hormone, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutically carriers for injectable compositions are well-known to those of ordinary skill in the art (see Pharmaceutics and Pharmacy Practice, J. B. Lippincott Co., Philadelphia, Pa., Banker and Chalmers, eds., pages 238–250 (1982), and ASHP Handbook on Injectable Drugs, Toissel, 4th ed., pages 622–630 (1986)). It is preferred that such injectable compositions be administered intramuscularly, intravenously, or intraperitoneally.

Topical formulations are well-known to those of skill in the art. Such formulations are suitable in the context of the present invention for application to the skin. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyloleate and isopropyl myristate are examples of suitable fatty acid esters.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkylimidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Such compositions can be formulated as intraocular formulations, sustained-release formulations or devices (see, e.g., U.S. Pat. No. 5,378,475). For example, gelantin, chondroitin sulfate, a polyphosphoester, such as bis-2-hydroxyethyl-terephthalate (BHET), or a polylactic-glycolic acid (in various proportions) can be used to formulate sustained-release formulations. Implants (see, e.g., U.S. Pat. Nos. 5,443,505, 4,853,224 and 4,997,652), devices (see, e.g., U.S. Pat. Nos. 5,554,187, 4,863,457, 5,098,443 and 5,725,493), such as an implantable device, e.g., a mechanical reservoir, an intraocular device or an extraocular device with an intraocular conduit (e.g., 100 microns–1 mm in diameter), or an implant or a device comprised of a polymeric composition as described above, can be used.

In addition to the co-administration of TRS and/or somotostatin, the present inventive method also can involve the co-administration of other pharmaceutically active compounds. For example, corticosteroids, e.g., prednisone, methylprednisolone, dexamethasone, or triamcinalone acetinide, or noncorticosteroid anti-inflammatory compounds, such as ibuprofen or flubiproben, can be co-administered. Similarly, vitamins and minerals, e.g., zinc, anti-oxidants, e.g., carotenoids (such as a xanthophyll carotenoid like zeaxanthin or lutein), and micronutrients can be co-administered. Neutralizing proteins to growth factors, such as a monoclonal antibody that is specific for a given growth factor, e.g., VEGF (for an example, see Aiello et al., *PNAS USA* 92: 10457–10461 (1995)), or phosphotyrosine (Dhar et al, *Mol. Pharmacol* 37: 519–525 (1990)), can be co-administered. Other various compounds that can be co-administered include inhibitors of protein kinase C (see, e.g., U.S. Pat. Nos. 5,719,175 and 5,710,145), cytokine modulators, an endothelial cell-specific inhibitor of proliferation, e.g., thrombospondins, an endothelial cell-specific inhibitory growth factor, e.g., TNF.alpha., an anti-proliferative peptide, e.g., SPARC and prolferin-like peptides, a glutamate receptor antagonist, aminoguanidine, an angiotensin-converting enzyme inhibitor, e.g., angiotensin II, calcium channel blockers, .psi.-tectorigenin, ST638, monosialoganglioside GM1, ticlopidine, neurotrophic growth factors, methyl-2,5-dihydroxycinnamate, an angiogenesis inhibitor, e.g., recombinant EPO, a sulphonylurea oral hypoglycemic agent, e.g., gliclazide (non-insulin-dependent diabetes), ST638 (Asahi et al., *FEBS Letter* 309: 10–14 (1992)), thalidomide, nicardipine hydrochloride, aspirin, piceatannol, staurosporine, adriamycin, epiderstatin, (+)-aeroplysinin-1, phenazocine, halomethyl ketones, anti-lipidemic agents, e.g., etofibrate, chlorpromazine and spinghosines, aldose reductase inhibitors, such as tolrestat, SPR-210, sorbinil or oxygen, and retinoic acid and analogues thereof (Burke et al., *Drugs of the Future* 17(2): 119–131 (1992); and Tomlinson et al., *Pharmac. Ther.* 54: 151–194 (1992)). Those patients that exhibit systemic fluid retention, such as that due to cardiovascular or renal disease and severe systemic hypertension, can be additionally treated with diuresis, dialysis, cardiac drugs and antihypertensive agents.

Following are examples which illustrate procedures for practicing the invention. These examples should not be construed as limiting. All percentages are by weight and all solvent mixture proportions are by volume unless otherwise noted.

EXAMPLE 1

Human Studies Evaluating Effects of Somatostatin Analogues and Somatostatin Analogue/Octreotide Treatment on Progression of Diabetic Retinopathy:

Methods

It has been recognized that Insulin-like Growth Factor 1 (IGF-1) mediates most of the anabolic effects of growth hormone, which in turn has been linked to diabetic vascular complications, including diabetic retinopathy.

A total of 39 patients with type I or type II diabetes and diagnosed with either severe non-proliferative DR or non-"high risk" proliferative DR were enrolled between 1991 and 1996 into Phase I or Phase II of the study. Subjects were recruited from patients treated for diabetes mellitus at the University of Florida Adult Endocrinology clinics and referrals from community retinal specialists. All patients provided written informed consent to participate in required study procedures. Volunteers in both phases of the study were randomized to receive conventional diabetes management alone (control group) or octreotide treatment with conventional diabetes care (OCT group). Octreotide was administered via subcutaneous injection 4 times daily or via continuous subcutaneous infusion with doses individually adjusted to the highest tolerated somatostatin analogue levels. The intent was to increase the dose of octreotide until serum IGF-1 was decreased to the hypopituitary range of 75 ng/mL or drug related adverse effects limited octreotide dosing. The open label study was designed to continue for 15 months with early termination required if both of the patient's eyes showed disease progression requiring laser photocoagulation during the 15-month dosing period. It was expected that approximately 35 to 50% of the control group would progress to photocoagulation within the 15-month period (The Diabetic Retinopathy Study Research Group: Indications for photocoagulation treatment of diabetic retinopathy: Diabetic Reinopathy Study Report No. 14. Int. Opthalmol. Clin. 27:239 (1987)).

Subjects were evaluated at monthly intervals for ocular changes using procedures established in the Early Treatment Diabetic Retinopathy Study (ETDRS) trial (Techniques for scatter and local photocoagulation treatment of diabetic retinopathy. Early Treatment Diabetic Retinopathy Study Report No. 3. The Early Treatment Diabetic Retinopathy Study Research Group. *Int Ophthalmol Clin.* 27:254–64 (1987)). Ocular examination included fluorescein angiograms and stereoscopic fundis photographs using seven standard photographic fields. Each field was 30 degrees with the first 2 fields centered on the disc and macula. The other fields imaged the surrounding retina. Photographs were assessed for severity of retinopathy using an extension of the modified Airlie House classification scheme. Severe non-proliferative DR required the presence of at least 3 of the following characteristics: cotton wool patches, venous beading, intraretinal microvascular abnormalities (IRMA) or extensive retinal hemorrhages. Inclusion criteria also required understanding the study protocol and willingness to participate in required study procedures. Exclusion criteria included: current use of tobacco products, regular medication other than prescribed antidiabetic agents and thyroxine, history of psychiatric illness, illicit drug use, sitting diastolic blood pressure values greater than 50 mm Hg, serum creatinine clearance below 30 ml/min, and a body mass index that differed more than 20% from normal published ranges for the subject's height and sex.

Sixteen subjects with Type I diabetes participated in and completed the Phase-I protocol, with 8 patients randomly assigned to conventional diabetes management and 8 patients assigned treatment with maximally tolerated doses of octreotide in conjunction with routine diabetes management.

Initial octreotide doses of 500 µg/day were escalated based on IGF-1 levels to a maximum of 3000 µg/day during the 15-month treatment period. The range of maximally tolerated octreotide doses used throughout the 15-month treatment period was 600 to 3000 µg/day. The Phase protocol included a 5-day evaluation period with patients confined to the clinical research unit at study initiation. Octreotide treated patients were monitored for response to the initial 500 µg/day dose of octreotide (administered as a constant subcutaneous infusion). GH secretion was quantified from area under the serum concentration versus time curve (AUC) for blood samples collected every 2 to 4 hours throughout a 24-hour period.

Patient selection criteria for Phase II utilized the same inclusion and exclusion criteria from Phase I, except the protocol was expanded to include patients with either Type I or Type II diabetes. Phase II did not include confinement to the clinical study center and was conducted in the investigators' patient clinics. A total of 23 patients completed the 15-month Phase II protocol between 1993 and 1997. Twelve patients were randomized to the control group with conventional diabetes management. The treatment group included 11 patients given continuous or 4 times daily subcutaneous octreotide at maximally tolerated doses and concomitant thyroid hormone. Thyroid hormone doses (oral Synthroid®) ranged from a minimum of 100 µg/day to a maximum of 150 µg/day of levothyroxine. Maximally tolerated octreotide doses ranged from 200 to 5000 µg/day. Mean duration of diabetes did not differ between patients assigned to control (18.4±4.7 years) or treated (21.3±4.0 years) groups. Patients were assessed for ophthalmic changes at monthly intervals, clinical changes at 3-month intervals and biochemical parameters at the beginning and end of the 15-month trial. Hemoglobin $A_{1c}$ ($Hb_{A1c}$) was monitored as an index of glycemic control. Demographics for the patients in Phase II are listed in Table 1.

Statistics: Results from Phase I and Phase II of study were separately evaluated with the aid of SAS (Statistical Analysis System) software. The two-tailed t-test was used to evaluate differences between the control and treatment groups for quantitative parameters. These parameters included: duration of diabetes at enrollment, AUCs for GH secretion (Phase I only), change in IGF-1, and change in HbA1c. The Kaplan-Meier product limit method was used to generate survival curves for time surviving without need for panretinal laser photocoagulation (PRP) for each eye. The difference between treatment groups was compared using a log rank non-parametric test of significance between the curves. The Fisher's exact test was used to test for significant differences in the incidence of PRP between the treated and control groups.

TABLE 1

Patient Demographics for Subjects enrolled in Phase II.

| Patient Initial/sex | Diabetes Type | Years of Diabetes | Levothyroxine Dose (µg/day) |
|---|---|---|---|
| Treatment Group - OCT + $T_4$ | | | |
| JR/M | I | 18 | 100 |
| SS/F | I | 10 | 200 |
| AJ/M | I | 15 | 125 |
| MJ/M | I | 20 | 150 |
| MO/F | I | 22 | 125 |
| HK/M | I | 24 | 100 |
| DS/F | I | 19 | 150 |
| HD/F | II | 21 | 125 |
| BW/F | II | 24 | 150 |
| WD/M | II | 12 | 100 |
| JA/M | II | 15 | 125 |
| Mean | | 18.3 | |
| SD | | 4.7 | |
| Treatment Group - Control | | | |
| CW/M | I | 20 | 200 |
| DA/F | I | 21 | 150 |
| GP/M | I | 15 | 100 |
| KW/M | I | 24 | none |
| IG/M | I | 26 | none |
| BM/M | I | 20 | 125 |
| JH/F | II | 24 | none |
| MS/M | II | 27 | 100 |
| HW/M | I | 18 | 125 |
| JS/F | I | 21 | 100 |
| KS/F | II | 25 | none |
| LG/F | II | 15 | none |
| Mean | | 22.1 | |
| SD | | 4.0 | |

Results

Figure 1:
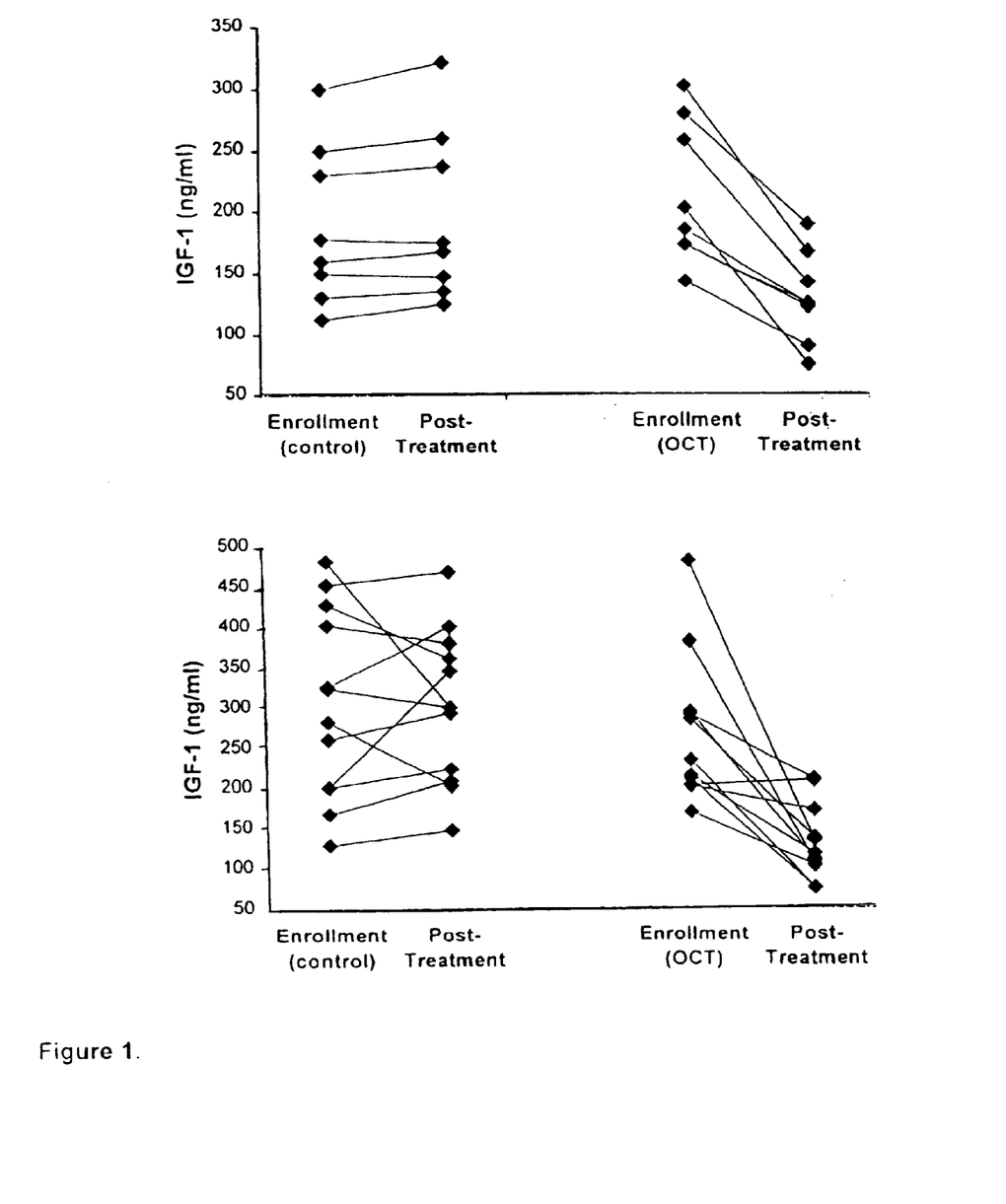
FIG. 1 shows a graph which relates to individual IGF-1 values for conventionally managed (control) and octreotide treated (OCT) subjects enrolled in Phase I (upper panel) and Phase II (lower panel) in accord with the procedures disclosed herein.

Phase I: Octreotide treatment significantly decreased IGF-1 levels from 241±58 ng/ml at study enrollment to a mean of 130±38 ng/ml measured at the end of treatment. All patients enrolled completed the 15-month study protocol. The change in IGF-1 during treatment was significantly different compared to the relatively stable values found in control subjects with conventional diabetes management ($p<0.05$). However, only 1 of 8 patients receiving maximally tolerated peptide doses ranging from 600 to 3000 µg/day had IGF-1 decreased into the hypophysectomized range of 75 ng/ml. Individual changes in IGF-1 at study enrollment and study termination are shown in FIG. 1. Mean IGF-1 values did not differ over the course of the 15-month study for conventionally managed patients. Mean IGF-1 measured in plasma was 188±65 ng/ml at enrollment and 196±70 ng/ml at completion of the Phase protocol for control subjects. Glycemic control, reflected in mean HbA1c values after at least 3 months of study, was significantly improved ($p<0.05$) with octreotide treatment (6.4%±0.9%) compared to mean HbA1c values with conventional management (8.1%±1.8%). Improved glycemic control was associated with a 29% decrease in insulin requirements and an 82% improvement in proteinuria measured for the octreotide treated group that was significantly different from the conventionally treated group ($p<0.05$). Initial 500 µg/day doses of octreotide significantly decreased mean GH secretion that was shown by a mean 33% decrease in 24 hour AUC parameters for GH measured on day 5 of peptide treatment compared to control ($p<0.05$).

Figure 3:
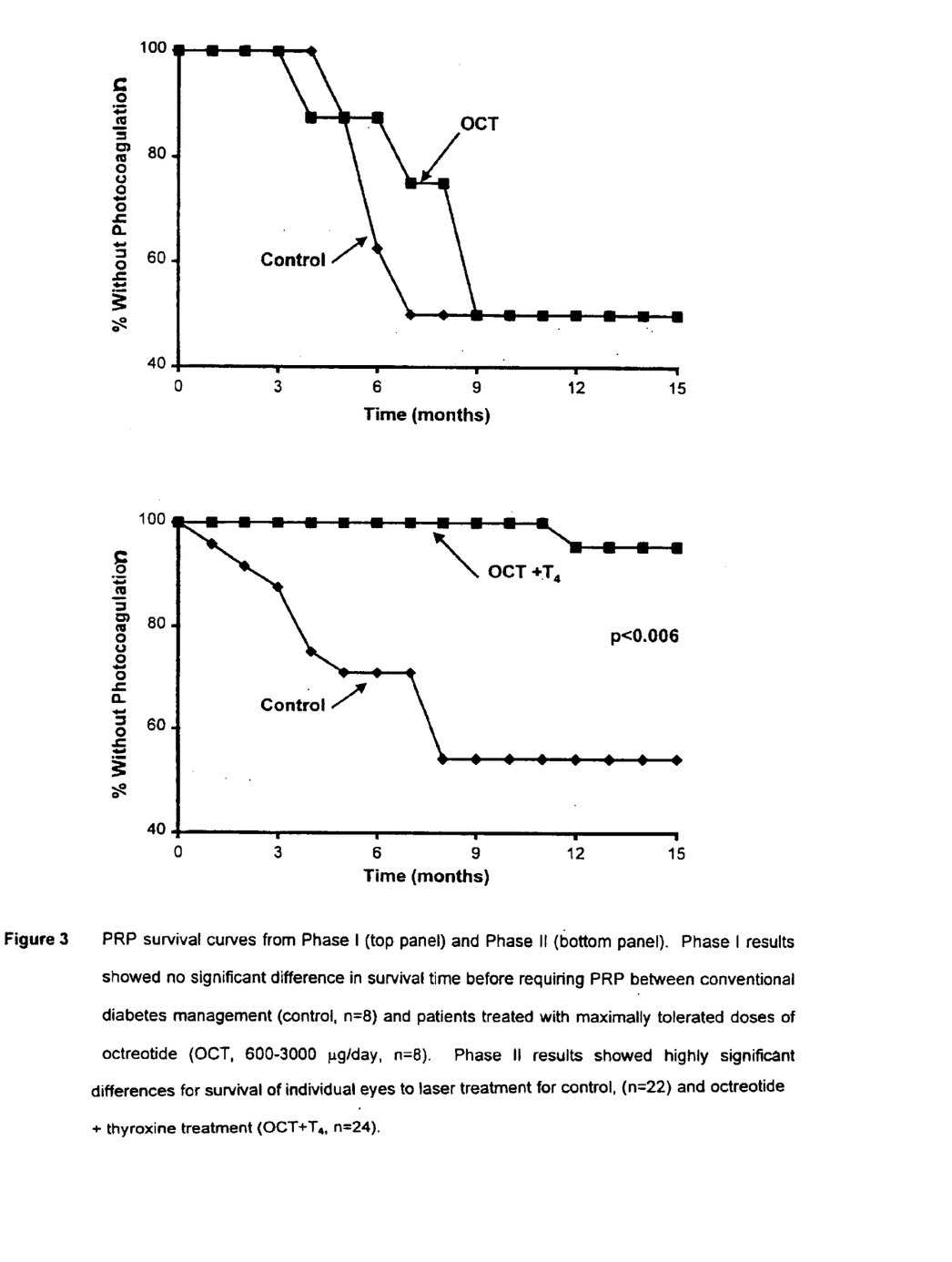
FIG. 3 PRP survival curves from Phase I (top panel) and Phase II (bottom panel). Phase I results showed no significant difference in survival time before requiring PRP between conventional diabetes management (control, n=8). Phase II results showed highly significant differences for survival of individual eyes to laser treatment for control, (n=22) and octreotide+thyroxine treatment (OCT+$T_4$), n=24).

Survival curves for the time surviving without PRP are shown in FIG. 3 (upper panel). Four patients in each group required PRP during the 15-month study. The mean time of 6.0 months required for disease progression to laser surgery in control subjects was not different from the mean of 8.5 months in octreotide treated patients.

Phase II: In contrast to the results from Phase I studies, there was a highly significant difference detected for the PRP-free time profiles between octreotide treated and control groups ($p<0.006$). As graphically shown in FIG. 3 (lower panel), only 1 of 22 eyes from octreotide+thyroxine treated patients required PRP during month 12 of the study, while 9 of 24 eyes in conventionally managed patients required PRP between 1 and 8 months of study. These differences could not be attributed to thyroxine treatment alone since 3 of the 7 control patients receiving thyroxine at doses ranging from 100 to 200 µg/day to manage hypothyroidism required PRP. There were significant effects of octreotide on the incidence of PRP when only control subjects managed with thyroxine were included in the analysis ($p<0.024$).

Figure 2:
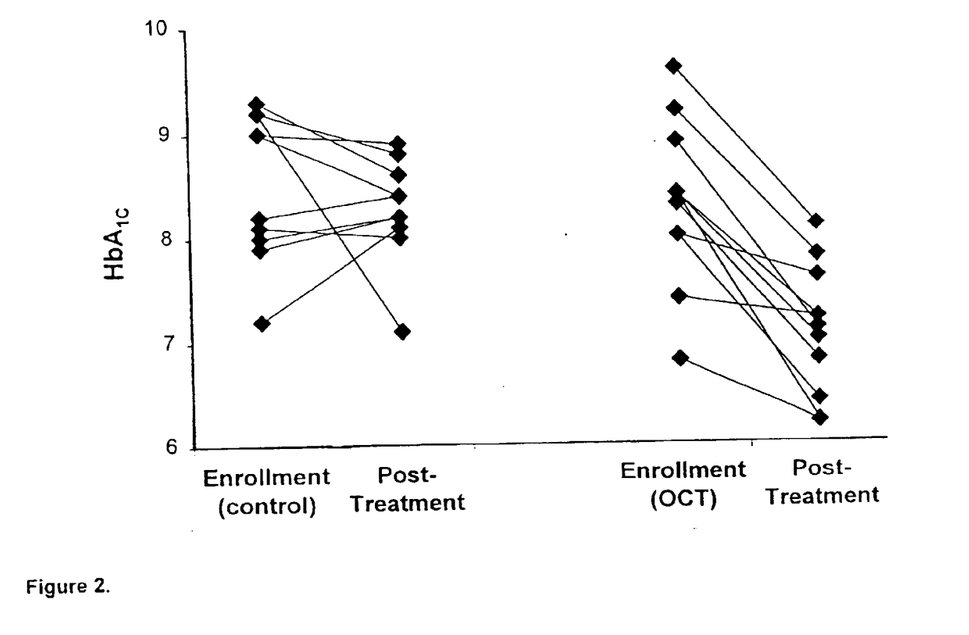
FIG. 2 shows individual glycosylated hemoglobin ($HbA_{1C}$) values for subjects enrolled in Phase II receiving conventional diabetes management (control) and octreotide treatment (OCT). Glycosylated hemoglobin was measured before treatment (enrollment) and at study termination (post-treatment).

As shown in FIG. 1, individual IGF-1 decreases occurring between the beginning and end of the 15-month study for octreotide treated patients were similar in magnitude between Phase I (FIG. 1, upper panel) and Phase II (FIG. 1, lower panel) study patients. Two of 11 patients in the octreotide+$T_4$ treatment group in Phase II had IGF-1 suppressed to hypophysectomized levels. IGF-1 values were unchanged over the treatment period in conventionally managed patients with means of 305±118 ng/ml at enrollment and 303±94 ng/ml at study termination. In contrast, IGF-1 was significantly suppressed from mean value of 270±93 ng/ml at the beginning of octreotide treatment to 132±47 ng/ml at study termination ($p<0.05$). There was no difference in IGF-1 levels before drug treatment between treated and untreated patients. FIG. 2 shows a similar profile of improved HbA1c in octreotide treated patients. Mean HbA1c significantly decreased from 8.6±0.8% to 7.2±0.6% for the octreotide+T4 group, but was unchanged in controls that had a mean initial value of 8.4:t0.8% and a final mean value of 8.3±0.5%.

The results from this study show that chronic octreotide treatment may retard development of "high risk" retinal disease for patients with advanced DR when administered in combination with thyroid hormone replacement therapy. Treatment with maximally tolerated doses of octreotide in combination with replacement doses of levothyroxine for 15 months showed a significantly lower incidence of disease progression compared to conventional diabetes management. Disease progressed to require PRP in only 1 of 22 eyes from patients treated with combination octreotide and thyroid hormone replacement compared to 9 of 24 eyes from patients treated with conventional diabetes management. Five of the 9 eyes that required PRP in the group of controls were receiving thyroid hormone replacement as a component of conventional endocrine management. Treatment with maximally tolerated octreotide was not effective in retarding progression of DR in the absence of thyroid hormone replacement therapy, since 4 of 8 patients in the control and in the octreotide groups required retinal surgery during 15 months of the Phase I study. The results implicate a role for thyroid hormone in mediating the antiproliferative effects of somatostatin analogues on retinal neovascularization.

Interestingly, a trial examining the ability of long term octreotide treatment to improve early DR identified mild hypothyroidism in patients infused for one year with 400 μg/day of the somatostatin analogue, but found no evidence for clinical significance of the hypothyroidism (Kirkegaard et al, Acta Endocrinol (Copenh) 122:766–72 (1990)). Results of their trial with early DR and our Phase I trial were nearly identical in finding no difference between retinal disease in conventionally managed patients and octreotide treatment.

Hypothyroidism could impair the antiproliferative effect of somatostatin through several mechanisms that may be clinically relevant for treatment with octreotide or other long acting analogues. At least three mechanisms have been proposed for the antiproliferative effects of somatostatin (Breeman et al, Studies on radiolabeled somatostatin analogues in rats and in patients. Q J Nucl Med; 40:209–20 (1996)). Somatostatin receptor activation stimulates tyrosine phosphatase and may reverse the growth promotion of the tyrosine kinase group of oncogenes to effect antiproliferative cell signaling. In vitro studies showed that the somatostatin analogues activate protein tyrosine phosphatases and therefore function at the biochemical level by promoting inactivation of the autophosphorylated growth factor receptor (Colas et al, Stimulation of a membrane tyrosine phosphatase activity by somatostatin analogues in rat pancreatic acinar cells. Eur J Biochem 207:1017–24 (1992). Leszczynski et al, Rat heart smooth muscle cells express high and low affinity receptors for somatostatin-14, which are involved in regulation of cell proliferation. Life Sci. 53:1663–1674 (1993)). Somatostatin may directly inhibit steps in the cascade of events resulting in angiogenesis. Our studies conducted in rapidly proliferating human retinal endothelial cells that were stimulated with IGF-I and b-FGF in vitro demonstrated direct inhibitory effects of octreotide in these cells (Grant et al, Inhibition of IGF-I and b-FGF stimulated growth of human retinal endothelial cells by the somatostatin analogue, octreotide: a potential treatment for ocular neovascularization. Regul Pept 48:267–278 (1993)). Alternatively, the antiproliferative effects of somatostatin have been attributed exclusively to inhibiting secreted GH, IGF-1 and other secreted hormones involved in growth. Our clinical results showing similar degree of IGF-1 inhibition in patients receiving octreotide with thyroid hormone (Phase II) or octreotide alone (Phase I) suggest that the degree of secreted hormone suppression measured in the circulation does not account for improved efficacy of octreotide in DR.

Vitreous levels of IGF-I better reflect the local levels of growth factors seen by retinal tissue. Our earlier study measured IGF-1 from vitreous samples collected in 23 diabetic patients with proliferative DR compared with age-matched control values (Grant et al, Diabetes 35:416–20 (1986)). A 3-fold increase was observed in the DR samples compared with controls. IGF-I secretion was augmented by basic fibroblast growth factor in cultured human retinal endothelial cells, which supports a paracrine role (Grant, et al. (1993), supra). The finding that vitreous concentrations of IGF-I are significantly increased in diabetics with neovascularization was independently confirmed (Meyer-Schwickerath et al, J Clin Invest 92:2620–5 (1993)). Studies in animal models of ocular neovascularization indicate the significance of GH and IGF-1 in retinal disease. Intravitreal IGF-1 administration, but not heat inactivated protein, can reproduce several microvascular abnormalities that are found in DR including: increased basement membrane thickening, severe hyperemia with vascular engorgement, tortuosity, intraretinal hemorrhage and endothelial cell proliferation (Grant et al, Ann Ny Acad Sci 692:230–242 (1993) Oanis et al, Ophthalmology 104:1661–9 (1997)). In apparent contrast to the simple hypothesis that increased IGF-I mediates aberrant neovascularization, several studies showed that circulating IGF-I levels are inappropriately low in most patients with Type I diabetes given their higher-than-norma GH levels (Amiel et al, Diabetes 33:1175–9 (1984); Tan et al, J. Clin. Endocrinol Metab. 63:651–655 (1986)). This observation in IDDM patients is due in part to lack of portal insulin, which stimulates hepatic IGF-1 secretion. The ability of IGF-I to lower glucose and abnormal GH/IGF-I/IGF binding protein (IGFBP) system identified in diabetics led to use of recombinantly produced IGF-1 (rIGF-I) to treat hyperglycemia in diabetics. However, the doses of rIGF-I required to improve hyperglycemia may be limited by adverse effects. Among the most serious of these adverse effects from rIGF-I treatment is progression of DR (Kolaczynski et al, Ann Intern Med 120:47–55 (1994)). Langford et al, Eur J Clin Invest 23:503–516 (1993)). Cusi et al, Diabetes Rev. 3:206–236 (1995)). A recent report identified two cases of retinal changes mimicking DR in non-diabetic patients treated with GH dosing regimens that would be expected to increase IGF-1 (Koller et al, J Clin Endocrinol Metab 83:2380–3 (1998)).

Retinal neovascularization and chronic retinal edema associated with severe DR threaten vision. PRP is currently the only accepted treatment option for severe "high risk" DR and is thought to effectively block aberrant capillary vessel formation by destroying retinal tissue, which is the source of growth factors implicated in angiogenesis. Although recent elegant studies in various animal models suggest that selectively altering just one of the growth factors involved in angiogenesis would effectively retard neovascularization, no effective therapeutic alternatives to retinal tissue destruction have been identified (Aiello et al, *Diabetes* 46:1473–80 (1997) Smith et al, *Science* 276:1706–1709 (1997)).

The teachings of all the references cited throughout this specification are incorporated herein by this reference to the extent that they are not inconsistent with the teachings herein. It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of treating or preventing the onset of diabetic retinopathy in a patient comprising administering somatostatin to said patient and co-administering a thyroid-related substance.

2. The method of claim 1, wherein said somatostatin is octreotide, lanreotide, vapreotide, MK 678, L-363-377, L-797,591, L-779,976, L-796-778, L-803,087, L-817,818, or combinations thereof.

3. The method of claim 1, wherein said thyroid related substance is thyroid hormone, thyroxine, thyrotropin, thyroid stimulating hormone, or analogues or, pharmaceutically acceptable salts or derivatives thereof that have similar biological functionality or effect in the body.

4. A composition useful for treating or preventing the onset of DR comprising a mixture of somatostatin and a thyroid-related substance.

5. A kit comprising at least one container having somatostatin and a thyroid-related substance disposed therein.

6. The kit of claim 5 further comprising a syringe for administration of the somatostatin and thyroid-related substance.

7. The kit of claim 6 wherein at least one container is one or more syringes having somatostatin and thyroid-related substance disposed in either one syringe as a mixture or in separate syringes.

8. The kit of claim 5 wherein the somatostatin and thryroid-related substance is in a form suitable for oral administration.

9. A method of treating or preventing the onset of DR comprising administering somatostatin and co-administering a thyroid-related substance, wherein the dosage of said somastostatin and said thyroid-related substance is of an amount such that any synergistic effect of said administering or co-administering is optimized.

10. An article of manufacture comprising somatostatin and thyroid-related substance.

11. The article of manufacture of claim 10 in the form of a solid or liquid.

12. A method of treating or preventing the onset of diabetic retinopathy comprising assaying a group of somatostatin analogues for their ability to bind to a sstr2 somatostatin receptor; selecting one or more analogues having high affinity to said sstr2 somatostatin receptor; and administering said one or more selected analogues to a patient in need thereof; and co-administering a thyroid-related substance.

13. The method of claim 12 wherein said high affinity comprises a $K_i$, value in nanomoles of about 2 or less.

14. A method of treating or preventing DR in a patient comprising identifying whether said patient is susceptible to developing DR; administering somatostatin to said individual; and co-administering a thyroid related substance.

15. The method of claim 14, wherein said thyroid related substance is thyroxine delivered in an amount of 100–200 μg a day.

* * * * *